US012653390B2

(12) United States Patent
Biehe et al.

(10) Patent No.: US 12,653,390 B2
(45) Date of Patent: Jun. 16, 2026

(54) LIGHT MODULE FOR AN ENDOSCOPIC SYSTEM, USE OF A LIGHT MODULE, AND ENDOSCOPIC SYSTEM

(71) Applicant: AMBU A/S, Ballerup (DK)

(72) Inventors: Snorre Biehe, Roskilde (DK); Jacob Drasbæk, Herlev (DK)

(73) Assignee: AMBU A/S, Ballerup (DK)

( * ) Notice: Subject to any disclaimer, the term of this patent is extended or adjusted under 35 U.S.C. 154(b) by 290 days.

(21) Appl. No.: 18/373,740

(22) Filed: Sep. 27, 2023

(65) Prior Publication Data

US 2024/0099569 A1 Mar. 28, 2024

(30) Foreign Application Priority Data

Sep. 28, 2022 (EP) .................................... 22198242

(51) Int. Cl.
*A61B 1/06* (2006.01)
*A61B 1/00* (2006.01)
(Continued)

(52) U.S. Cl.
CPC ........ *A61B 1/0684* (2013.01); *A61B 1/00096* (2013.01); *A61B 1/00126* (2013.01); *A61B 1/0638* (2013.01); *A61B 1/0669* (2013.01); *A61B 1/128* (2013.01); *A61B 1/00045* (2013.01); *A61B 1/07* (2013.01)

(58) Field of Classification Search
CPC .............. A61B 1/0684; A61B 1/00096; A61B 1/00126; A61B 1/00128; A61B 1/0638; A61B 1/07; A61B 1/128; A61B 1/00045; A61B 1/00165; A61B 1/0669;
(Continued)

(56) References Cited

U.S. PATENT DOCUMENTS

| | | | |
|---|---|---|---|
| 6,260,994 B1 | 7/2001 | Matsumoto et al. | |
| 6,918,693 B2 | 7/2005 | Ota et al. | |
| | (Continued) | | |

FOREIGN PATENT DOCUMENTS

| | | |
|---|---|---|
| DE | 2013090 A1 | 9/1971 |
| EP | 1148810 B1 | 11/2005 |
| JP | 2003-047591 A | 2/2003 |

OTHER PUBLICATIONS

European Search Report for EP Patent Application No. 22198242.4, Issued on Mar. 6, 2023, 7 pages.

*Primary Examiner* — Michael J Carey
*Assistant Examiner* — Olivia Grace Starkey
(74) *Attorney, Agent, or Firm* — Faegre Drinker Biddle & Reath LLP

(57) ABSTRACT

A light module for an endoscopic system and including: a coupling element; at least one light guiding element connected to the coupling element and configured to guide light towards a distal tip unit of an endoscope included in the endoscopic system; a plurality of light emitting devices connected to the coupling element and configured to emit light; a plurality of collimator elements or portions configured to collimate the light emitted by the plurality of light emitting devices; a plurality of mirror elements or portions configured to reflect the light emitted by the plurality of light emitting devices and collimated by the plurality of collimator elements or portions towards and into the at least one light guiding element.

19 Claims, 5 Drawing Sheets

(51) Int. Cl.
  *A61B 1/12* (2006.01)
  *A61B 1/07* (2006.01)

(58) Field of Classification Search
  CPC .............. A61B 1/0661; A61B 1/00108; G02B
                            23/2469; G02B 23/2453
  See application file for complete search history.

(56) References Cited

U.S. PATENT DOCUMENTS

| | | | |
|---|---|---|---|
| 8,564,652 B2 | 10/2013 | Akiyama et al. | |
| 9,395,055 B2 | 7/2016 | Brukilacchio et al. | |
| 11,109,741 B1 | 9/2021 | Ubbesen et al. | |
| 11,583,164 B2 | 2/2023 | Ubbesen et al. | |
| 2002/0161282 A1 | 10/2002 | Fulghum | |
| 2017/0095144 A1* | 4/2017 | Tabata ................. | A61B 1/0684 |
| 2020/0154980 A1* | 5/2020 | Ben-Arye ............ | A61B 1/0684 |
| 2020/0188668 A1* | 6/2020 | Grossoehmichen ......................... | A61N 1/0541 |
| 2022/0031155 A1* | 2/2022 | Iwane .................. | A61B 1/0638 |
| 2023/0172433 A1* | 6/2023 | Levinson ........... | A61B 1/00066 600/109 |
| 2024/0115120 A1* | 4/2024 | Halderman .............. | A61B 1/04 |

* cited by examiner

LIGHT MODULE FOR AN ENDOSCOPIC SYSTEM, USE OF A LIGHT MODULE, AND ENDOSCOPIC SYSTEM

CROSS-REFERENCE TO RELATED APPLICATIONS

This application claims priority from and the benefit of European Patent Application No. EP22198242.4, filed Sep. 28, 2022; the disclosure of the aforementioned application is incorporated by reference herein in its entirety.

TECHNICAL FIELD

The present disclosure relates to a light module for an endoscopic system, a use of a light module in an endoscopic system, and an endoscopic system.

BACKGROUND

Endoscopes are used for visual examination and diagnosis of hollow organs and body cavities, as well as to assist in surgery, e.g. for a targeted tissue sampling. Endoscopes include reusable and disposable, i.e. single-use, endoscopes. Endoscopes include specialized instruments such as bronchoscopes, arthroscopes, colonoscopes, laparoscopes, gastroscopes, duodenoscopes, ureteroscopes, and, generally, medical devices with an insertable elongate portion having, at a distal end thereof, a light emitter and an image sensor.

An endoscope usually comprises a handle via which an operator can hold and control the endoscope. An insertion cord comprising an insertion tube, an actively bendable bending section and a distal tip unit are usually connected to the handle. The insertion cord is configured to be inserted into the hollow organs and body cavities of a patient. The distal tip unit usually contains a light emitting device like a light-emitting diode or a light guiding element like a fiber optic light guide connected to a proximal source of light and an imaging device comprising e.g. an image sensor and a lens system so that the patient's body cavity can be illuminated and viewed by the operator, e.g. via a monitor usually provided in a display unit connected to the endoscope. The display unit may further comprise an image processing device which can communicate with the image sensor via a communication bus. Images captured by the image sensor may be transferred via the communication bus to the image processing device, where they are processed. The endoscope and the display unit in combination form an endoscopic system.

Light emitting diodes in the distal tip unit of the insertion cord of the endoscope are provided to illuminate the patient's body cavity. To further improve the quality of the camera images and/or videos, e.g. the resolution of the camera images and/or videos, it is desirable to increase a sensor size of the image sensor and to provide higher frame rates. An increased sensor size and higher frame rates may, however, raise the requirements for illumination, which means that it would be desirable to increase a power of the light emitting diodes provided in the distal tip unit of the endoscope. Powerful light emitting diodes, however, generate more heat. As the heat is emitted by the light emitting diodes provided in the distal tip unit of the endoscope in close proximity to tissue to be examined, the heat may exceed an acceptable heat limit and may cause physical damage to the examined tissue. Cooling of the light emitting diodes provided in the distal tip unit is difficult in light of the limited available space in the distal tip unit of the endoscope.

Further, when providing a plurality of light emitting diodes in the distal tip unit of the endoscope, it may be desirable to mix different colored light. However, when the examined tissue is quite close to the light emitting diodes, the colored light might not adequately mix so that the intensity and chromaticity of the mixed light does not appear spatially uniform to the operator of the endoscope.

Light modules may be provided in external light boxes. Xenon lamps or high powered light emitting diodes in such external light boxes can be used. A light guiding element extends from the external light box through the endoscope to the distal tip unit. Light from xenon lamps may be filtered to achieve specific wavelengths in order to provide colored light in the patient's body cavity. Providing the light module in an external device may simplify cooling of the light source. Further, in case the light source comprises a number of light emitting diodes, the colored light emitted by the number of light emitting diodes may be mixed in the light guiding element and may exit the light guiding element as spatially uniform light. However, the coupling efficiency between the light emitting device and the light guiding element is often poor in related art solutions so that loss of light occurs, i.e. a low amount of light reaches the distal tip unit and can be emitted for illuminating the patient's body cavity. In one example of such related art solutions having poor coupling efficiency between the light emitting device and the light guiding element, light needs to cross an air gap, which is provided directly between the light emitting device and the light guiding element.

BRIEF DESCRIPTION OF THE DISCLOSURE

In view of the above-described problems, it is an object of the present disclosure to avoid or at least to mitigate the disadvantages of the related art, in particular to provide a light module for an endoscopic system that increases coupling efficiency, between a light emitting device and a light guiding element of the light module, and that reduces cost in view of the increased coupling efficiency or otherwise.

The present disclosure relates to a light module for an endoscopic system. In one embodiment the light module comprises a coupling element connected to, preferably, one single light guiding element configured to guide light towards a distal tip unit of an endoscope comprised in the endoscopic system. The light module further comprises a plurality of light emitting devices connected to the coupling element and configured to emit light, a plurality of collimator elements or portions configured to collimate the light emitted by the plurality of light emitting devices and a plurality of mirror elements or portions configured to reflect the light emitted by the plurality of light emitting devices and collimated by the plurality of collimator elements or portions towards and into the at least one light guiding element. The light module is designed such that each light emitting device of the plurality of light emitting devices emits its light through a specific or own collimator element or portion for each light emitting device onto a specific or own mirror element or portion for each light emitting device, and such that the plurality of mirror elements or portions reflects and directs the light emitted by the plurality of light emitting devices and collimated by the plurality of collimator elements or portions into the at least one light guiding element.

The light module is preferably designed such that the plurality of mirror elements or portions reflects and directs the light emitted by the plurality of light emitting devices and collimated by the plurality of collimator elements or portions into one single, i.e. common light receiving portion. The one single light receiving portion may be provided to receive and collect the light from all the provided mirrors. The one single light receiving portion may be a portion of the coupling element. The collected light may be directed or transferred into the one or more light guiding elements.

According to a preferred embodiment, the light module may be connected to one single light guiding element, i.e. not two, three or even more. In this case, the one single, i.e. common light receiving portion may be provided to receive and collect the light and the collected light may be directed or transferred into the one single light guiding element. Therefore, in case the light module is connected to only one light guiding element, the light reflected by the number of mirror elements or portions may be received and collected by the one single, i.e. common light receiving portion and directed to or into the one single light guiding element.

Alternatively, the light module may be connected to more than one, i.e. multiple light guiding elements. In this case, the common light receiving portion may be provided to receive and collect the light, wherein the collected light is directed or transferred into the multiple light guiding elements. Therefore, in case the light module comprises multiple light guiding elements, the light reflected by the number of mirror elements or portions may be received and collected by the one single, i.e. common light receiving portion and transferred to or into the multiple light guiding elements.

Said differently, according to the present disclosure the light module may comprise one collimator element or portion and one mirror element or portion for each light emitting device. The light emitted by each light emitting device is emitted towards the respective specific or own mirror element or portion for each light emitting device. On the way towards the mirror element or portion, the light is collimated by the respective specific or own collimator element or portion for each light emitting device. The mirror element or portion reflects the collimated light towards the common light receiving portion. The received light may then be directed or transferred into the at least one light guiding element. The light guiding element guides the reflected light to the distal tip unit of the endoscope comprised in the endoscopic system. The light may exit the distal tip unit through an optical element such as a diffuser or a lens.

The coupling element of the light module may comprise a coupling portion for coupling the at least one light guiding element to the coupling element, in particular to the common light receiving portion.

The collimator element or portion, in the context of the present disclosure, is not limited to an element or portion collimating light such that the light rays passing through the collimator element or portion are parallel when leaving the collimator element or portion. According to the present disclosure, "collimating light" may mean that light rays may be, in particular slightly, focused on a focal area. A converging or convex lens may also be understood as the collimator element or portion in this context. In general, a portion or element having a geometry or design that avoids the divergence of light and that enhances or promotes the convergence of light may be included in the term collimator element or portion in the context of the present disclosure.

The plurality of light emitting devices may be a plurality of light emitting diodes (LEDs). The use of LEDs as light emitting devices comprises a number of advantages. In particular, LEDs can emit light of a specific wavelength, e.g. colored light of a specific wavelength. The usage of colored light may improve the visibility of specific features in a captured image. LEDs may generate less heat during usage compared to e.g. xenon lamps. Furthermore, LEDs are advantageously cost-effective and do not need much power.

Preferably, the at least one light guiding element is a light fiber or a light guide. The use of light fibers or light guides in light transfer is well known. Light fibers or light guides may be formed or designed to avoid light loss during light transmission. A light guiding element may comprise a bundle of thin strands of a drawn substrate, such as glass or polymer. The at least one light guiding element may comprise more than one bundle of the strands. Because the bundles of strands may extend through the flexible insertion cord of the endoscope, which may have a diameter smaller than 3.0 mm, and even smaller than 2.8 mm, multiple bundles may be desirable to increase the flexibility of the insertion cord, by separating the bundles and perhaps placing them on a bending plane of the insertion cord, on which the live hinges lie, without increasing its cross-section. A light guiding element may also comprise one strand, which is typically larger in diameter than the strands in the bundle.

The light module comprising a plurality of light emitting devices means that the light module may comprise any number of light emitting devices that is greater than one.

Preferably, the plurality of mirror elements or portions are spherical, elliptical or parabolic mirror elements or portions. The spherical, elliptical or parabolic mirror elements or portions may focus the light after reflection onto a focal point or area of the mirror elements or portions. Therefore, the light intensity in the focal point or area may increase due to the mirror elements or portions. In general, the mirror elements or portions may increase the light transfer efficiency between the light emitting devices and the at least one light guiding element. Combining light from multiple light emitting devices into a common light receiving portion of the coupling element can also generate the desired illumination even if the light transfer efficiency is not substantially perfect. As used herein, a mirror is a reflective surface that reflects a clear image. Typically, a mirror comprises a substrate coated with a metal amalgam. The substrate typically protects the reflective surface and is therefore transparent. A typical mirror comprises a polymer or glass coated with a metallic coating which is protected by the thickness of the substrate. Other mirrors are comprised of polished metal, in which case the mirror is unprotected by the substrate and is therefore exposed. Thusly, a polymer coated with a metallic coating can form a mirror, regardless whether the metallic coating is exposed or protected by the polymer. In the present context, mirror elements or portions may be individual components, portions of individual components, reflective surfaces formed by coatings on portions of components, etc.

Preferably, a receiving portion of the at least one light guiding element is connected to the coupling element and the light is directed into the receiving portion of the at least one light guiding element, preferably via the one common light receiving portion of the coupling element. The receiving portion of the light guiding element may be positioned in the focal point or area of the mirror elements or portions. Thus, the receiving portion may receive the reflected light. As a result, a majority, preferably an entirety, of the reflected light may enter the light guiding element and may be transferred to the distal tip unit of the endoscope comprised in the endoscopic system.

To summarize, one aspect of the present disclosure is to emit light through a plurality of collimator elements or portions onto a plurality of mirror elements or portions by a plurality of light emitting devices and reflect and focus the light by the mirror elements or portions onto and/or into the at least one light guiding element. The at least one light guiding element may be a single light guiding element.

Collimation of the light emitted by the light emitting devices by means of the collimator elements or portions may increase a share of light reaching the mirror elements or portions and therefore may increase the light transfer efficiency between the light emitting devices and the mirror elements or portions. By reflecting the light emitted by the light emitting devices and focusing the light on the light guiding element, the transfer efficiency of the light transfer between the light emitting devices and the light guiding element may be further increased. The mirror elements or portions may be designed to focus the light on a focal point or area, namely a receiving portion of the light guiding element. Providing multiple light emitting devices that emit light into the at least one light guiding element makes it possible to increase or decrease the light quantity in the light guiding element by switching single light emitting devices on or off. The light emitting devices may emit light of different colors which may be mixed in the light guiding element e.g. depending on what color is desired. The length of the light guiding element may further ensure that the light of different colors is mixed in the light guiding element so as to appear as white light when exiting the distal tip unit of the endoscope comprised in the endoscopic system.

Preferably, the coupling element has a proximal side and a distal side. The plurality of light emitting devices and the at least one light guiding element may be provided on or may be connected to the distal side of the coupling element. The plurality of mirror elements or portions may be provided on the proximal side of the coupling element. The plurality of light emitting devices may be configured to emit light in a proximal direction towards the plurality of mirror elements or portions. The plurality of mirror elements or portions may be configured to reflect the light in a distal direction towards the at least one light guiding element, in particular towards the one common, i.e. single light receiving portion for the one or more light guiding elements.

According to the present disclosure, "distal" means in a direction towards a patient away from an operator, and "proximal" means in a direction towards the operator away from the patient. The distal side of the coupling element is thus to be understood as the side that is closer to the distal tip unit, whereas the proximal side of the coupling element is to be understood as the side that is farther away from the distal tip unit.

The plurality of light emitting devices may emit light in the direction of the plurality of mirror elements or portions. Preferably, the plurality of light emitting devices are attached to an outer surface of the coupling element. The mirror elements or portions may be positioned on the side of the coupling element which is opposite with respect to the side of the light emitting devices. Therefore, the mirror elements or portions may reflect the emitted light in a direction, which is opposite to a direction in which the light was emitted by the light emitting devices. The plurality of mirror elements or portions may reflect the light towards the at least one light guiding element, preferably towards the one common light receiving portion. The at least one light guiding element may also be positioned on the distal side of the coupling element and therefore on the side opposite with respect to the mirror elements or portions. The mirror elements or portions may function as parabolic or elliptical or spherical mirror elements or portions focusing the light onto and/or into the light guiding element. The plurality of light emitting devices and the light guiding element may basically be positioned on the same side of the coupling element, which is the side opposite of the plurality of mirror elements or portions.

The plurality of collimator elements or portions may be provided on the distal side of the coupling element. Alternatively, the plurality of collimator elements or portions may also be provided closer to the mirror elements or portions. It is advantageous if the plurality of collimator elements or portions are positioned adjacent to, e.g. in close contact with the plurality of light emitting devices. Preferably, in close contact with the plurality of light emitting devices may be understood such that the plurality of collimator elements or portions are positioned directly adjacent to the light emitting devices. There is thus preferably no air gap between the plurality of light emitting devices and the plurality of collimator elements or portions. By arranging the collimator elements or portions adjacent to and/or in contact with the light emitting devices, it may be ensured that only minimal divergence of light and minimal light loss occurs.

According to a preferred embodiment, the coupling element may be a single and integral part. Additionally or alternatively, the coupling element may be transparent or translucent. Additionally or alternatively, the coupling element may be made from a polymer or plastic. However, other non-polymer materials are also conceivable. For example, it may be preferred if the coupling element is made from glass. According to an especially preferred embodiment, the coupling element may be a single and integral transparent or translucent polymer part. Therefore, the light may pass through the transparent or translucent polymer of the coupling element. The plurality of light emitting devices are preferably positioned on an outer surface and/or side of the coupling element and emit in the direction of the coupling element. The light emitted by the light emitting devices may enter the coupling element at positions where the plurality of collimator elements or portions are arranged and may pass there through and through the coupling element towards the plurality of mirror elements or portions. Manufacturing the coupling element as a single part preferably avoids assembly work, such as manual assembly work and costs. Furthermore, by the provision of the coupling element as a single part assembly tolerances e.g. in the form of tolerance chains, are avoided and the coupling element can be manufactured with high reproducibility. Especially a distance between the plurality of light emitting devices and the plurality of mirror elements or portions is as a result only subject to manufacturing tolerances. The dimensions of the coupling element may also define a distance between the plurality of mirror elements or portions and the at least one light guiding element. It may thus be ensured that the receiving portion of the at least one light guiding element is positioned in the focal point or area of the plurality of mirror elements or portions. Manufacturing tolerances of the integral coupling element are advantageously smaller than a tolerance chain resulting from an assembly of multiple components.

The coupling element is preferably a molded polymer part. Alternatively, the coupling element may also be made from glass or any other suitable material. Especially preferred the coupling element is an injection-molded polymer part. Injection-molding has the advantage of being a cost effective and highly automated manufacturing technique. However, the present disclosure is not limited to the coupling element being a single and integral part and the coupling element may also be assembled from two or more different parts. In this case, e.g. an air gap between the plurality of collimator elements or portions and the plurality of mirror elements or portions may exist and the coupling element may be rather designated as a housing.

Preferably, the collimator elements or portions are formed as collimator portions integrally provided in the coupling element. The collimator portions may e.g. be formed as integral windows or window portions in the coupling element. As the coupling element is preferably made or manufactured from a transparent or translucent material, the light may pass from the outside into the coupling element. At the entrance point of the coupling element, a spherical geometry, such as a convex spherical geometry, may be formed functioning as the collimator portion. The spherical geometry may be easily manufactured by injection molding of the coupling element and may collimate or focus the light entering the coupling element. The collimator portions may avoid or at least minimize loss of light due to divergence between the light emitting devices and the mirror elements or portions. The collimation may increase the share of the light reaching the respective mirror element or portion. By avoiding light loss by means of the collimator portions, the light transfer efficiency between the plurality of light emitting devices and the plurality of mirror elements or portions may be increased.

Preferably, the plurality of mirror elements or portions are formed as thin films and/or coatings. The thin films and/or coatings may be applied or attached on the coupling element. The thin films or coatings may be reflective. The mirror elements or portions are preferably manufactured by physical vapor deposition, provided on a portion or portions of the coupling element. The coating is preferably applied on a spherical, parabolic, and/or elliptical surface of the coupling element. The mirror elements or portions are therefore preferably manufactured so as to be an integral part of, i.e. integrally with the coupling element.

A convex and/or parabolic, spherical, and/or elliptical structure of the coupling element may be formed during manufacturing, in particular injection molding, of the coupling element. After the coupling element is finished, a reflective surface may be added to the convex structure to form the mirror elements or portions that function as the mirror elements or portions. The reflective surface is preferably deposited from the outside on the outer surface of the coupling element. The respective mirror elements or portions may focus the light on the common and/or shared focal point or area. The receiving portion of the light guiding element may be placed in the shared focal point or area of the mirror elements or portions. Therefore, a large share of the light reflected by the mirror elements or portions e.g. parabolic, spherical, and/or elliptical mirror elements or portions (more generally referred to "curved" surface), may reach the light guiding element. Loss of light may be reduced and the light transfer efficiency between the plurality of light emitting devices and the single light guiding element may be increased, particularly due to the shape and/or positioning of the mirror elements or portions.

However, the plurality of mirror elements or portions may also be manufactured using chemical vapor deposition or another coating technique. The plurality of mirror elements or portions may also be manufactured by applying a metal foil, as a further example of a thin film, on the coupling element.

Both the plurality of collimator elements or portions and the plurality of mirror elements or portions are preferably designed as integral parts of or integrally with the coupling element. By manufacturing the coupling element as a single integral part, additional assembly steps may be avoided and costs and manual labor may be reduced. Furthermore, the single piece coupling element may comprise no tolerance chain, as it would be the case with a modular assembly of multiple components to achieve the same function as the coupling element. Therefore, the coupling element is easy to manufacture and the respective distances between the light emitting devices and/or the collimator elements or portions and the mirror elements or portions, and especially between the mirror elements or portions and the light guiding element are reliably met. This may improve the light transfer between the light emitting devices and the light guiding element. Especially arranging the receiving portion of the light guiding element in the focal point or area of the mirror elements or portions may increase the transfer efficiency. The design of the coupling element may define the position of the light guiding element. Therefore, it may be ensured that the light guiding element is positioned in the focal point or area of the mirror elements or portions.

Preferably, the coupling element comprises a central axis and the at least one light guiding element, in particular a receiving portion of the at least one light guiding element connected to the coupling element, is arranged on the central axis. Therefore, the light guiding element is preferably positioned in a middle or center portion of the coupling element. Placing the light guiding element on the central axis may allow the coupling element to be symmetrical regarding the central axis. The coupling element may be designed to be rotationally symmetric regarding the central axis or axisymmetric regarding the central axis as a longitudinal axis.

The light guiding element may have a certain entry angle. The entry angle of the light guiding element may be understood as the angle at which light enters the light guiding element. A light guiding element usually has a critical entry angle or acceptance angle for light. The acceptance angle is the entry angle of the light that allows total reflection on the boundary between a core and a cladding of the light guiding element and therefore allows the light to pass through the light guiding element. Therefore, the entry angle of the light should be smaller than the acceptance angle so that the light can pass the light guiding element.

The core of the light guiding element may be manufactured from glass or a synthetic material like polymethylmethacrylate (PMMA) or polycarbonate (PC).

By reflecting the light emitted by the light emitting devices with the plurality of mirror elements or portions, the entry angle of the light rays into the light guiding element may decrease. If the entry angle of the light rays into the light guiding element is as small as possible, e.g. smaller than the acceptance angle of the light into the light guiding element, a risk of a loss of light during bending of the light guiding element may decrease. Bending of the light guiding element may occur during bending of the insertion cord. The bending of the light guiding element may change the acceptance angle and an increasing difference between the entry angle of the light and the acceptance angle may increase the acceptable bending of the light guiding element. An acceptable amount of bending of the light guiding element may be an amount of bending which allows light to still pass through the light guiding element without loss or light or with minimal loss of light. Therefore, the acceptable amount of bending of the light guiding element may be defined such that the acceptance angle is not smaller than the entry angle of the light.

Preferably, the light emitting devices are arranged around the central axis and are spaced in a circumferential direction of the coupling element. The light emitting devices are preferably positioned on the outer surface of the coupling element, each adjacent to or in contact with one of the collimator elements or portions. The light emitted by the light emitting devices may pass through the respective collimator elements or portions and may be emitted into the coupling element and towards the mirror elements or portions. By arranging the light emitting devices in a circle around the light guiding element, the required installation space for the light emitting devices is advantageously small. The distribution and/or circumferential space between the light emitting devices may avoid unwanted light interference.

Preferably, the light emitting devices are arranged on a first circle around the central axis. Additionally or alternatively, the light emitting devices may be equally spaced in the circumferential direction of the coupling element. This arrangement is advantageous with respect to the installation space needed for the light emitting devices. Furthermore, all light emitting devices may have the same distance to the light guiding element, which may result in the same light intensity of the light emitted by all light emitting devices in the light guiding element.

The first circle may be positioned in a way that the central axis of the coupling element runs through the center of the first circle.

Preferably, the light emitting devices are arranged symmetrically regarding a longitudinal axis of the coupling element. The longitudinal axis is preferably the central axis of the coupling element.

Preferably, the coupling element comprises a number of protruding arms or arm portions. The arms may protrude, preferably symmetrically, from a main body, e.g. a main body portion of the coupling element in different directions. Each protruding arm may comprise one light emitting device accommodation portion and one collimator element or portion. For each protruding arm, the coupling element may comprise one mirror element or portion. The mirror elements or portions are preferably positioned around the central axis of the coupling element. The light emitted by each light emitting device may be collimated by the respective collimator element or portion and may be reflected by the respective mirror element or portion towards the receiving portion of the light guiding element. The light emitting devices may emit light towards the respective mirror element or portion. The collimator elements or portions may collimate or focus the light before it reaches the mirror elements or portions. The mirror elements or portions may reflect the light towards the light guiding element and may focus the light.

In a preferred embodiment, the coupling element comprises exactly four protruding arms with four light emitting devices that are arranged symmetrically with respect to the longitudinal axis. Two of the four arms may protrude symmetrically in opposite directions respectively. The light emitting devices may have the same distances from their associated mirror elements or portions.

According to a preferred embodiment, the plurality of mirror elements or portions are arranged on a second circle around the central axis. The mirror elements and/or portions may be equally spaced in the circumferential direction of the coupling element or may be arranged directly adjacent to each other in the circumferential direction of the coupling element. Advantageously the coupling element comprises a respective mirror element or portion for each light emitting device. The mirror elements or portions may be arranged around the central axis in a way that the light emitted by each light emitting device reaches its respective associated mirror element or portion. Thus, each mirror element or portion may be oriented towards and/or in the direction of its respective associated light emitting device. The mirror elements or portions may be oriented to receive light from the respective light emitting device and reflect the light onto the light guiding element, i.e. the mirror elements or portions may face towards both the light emitting device and the light guiding element. The mirror elements or portions may have the same distance from the at least one light guiding element preferably resulting in the same light intensity reaching the receiving portion of the light guiding element for each light emitting device.

The second circle may be positioned in a way that the central axis of the coupling element runs through the center of the second circle. Furthermore, the second circle may be positioned concentrically to the first circle.

The mirror elements or portions may form a circle in a middle and/or center portion of the coupling element. The mirror elements or portions may be positioned adjacent, potentially directly adjacent, to each other. This design may allow to suitably accommodate the plurality of mirror elements or portions in the limited space of the coupling element.

Preferably, the light module further comprises cooling elements or portions arranged at or connected to the coupling element, the cooling elements or portions being configured to cool the light module, in particular the light emitting devices. Powerful or potent light emitting devices usually generate heat. The light emitting devices may be cooled using the cooling elements or portions to avoid overheating of the light module and/or reduce spot temperatures. If the light module is arranged inside the endoscope handle or interface or in an external display unit, there may be more and/or enough space available for the light module to implement the cooling elements or portions.

The cooling elements or portions may be provided at or connected to the distal side of the coupling element. The cooling elements or portions may preferably be arranged at or connected to the coupling element at portions of the coupling element where the light emitting devices are provided. The nearer the cooling elements or portions are placed with respect to the light emitting devices and/or the better the heat transfer to the cooling elements is, the better the cooling of the light module is.

The cooling elements or portions may comprise cooling ribs. The cooling elements or portions may be air-cooled. The cooling elements or portions may alternatively be cooled by a cooling fluid.

The cooling elements or portions may be attached to the coupling element by bolts. However, the cooling elements or portions for the light module can also be attached to the coupling element by another joining or fastening or fixation means. The cooling elements or portions may comprise finned heat-sinks and may be adhesively bonded to the coupling element or secured via the aforementioned bolts, or via press-fit, or a combination of various securement mechanisms. A heat-transfer paste may be applied between the heat-sink and the respective LED. Alternatively, one or more LEDs may be placed on one side of a metalic plate with one or more heat-sinks on the other side, forming a sub-assembly. The sub-assembly is then positioned onto the coupling element, potentially facilitating assembly of the light module.

Preferably, the light emitting devices are light emitting diodes (LEDs). Each light emitting device may comprise one, two, three or more LEDs e.g. one or more coloured light LEDs and/or white light LEDs. The plurality of light emitting devices may comprise at least one white light emitting diode and at least one colored light emitting diode. The user may thus switch between a mode of colored light and a mode of white light. Using colored light during examination of tissue may be advantageous since features in the tissue have better visibility when applying a light of a certain wavelength. Especially blue, green and red light can improve the visibility of relevant features in the examined tissue.

The present disclosure further relates to the use of a light module as described above in an endoscopic system comprising an endoscope having an endoscope handle or interface and a display unit connected to the endoscope. The light module may be provided e.g. in the endoscope handle or interface or in the display unit. Alternatively, the light module may be provided anywhere else in the endoscope, even in the distal tip unit, or in the endoscopic system. The at least one light guiding element may be configured to guide light from the light module towards the distal tip unit of the insertion cord of the endoscope. The use of the light module according to the present disclosure provides a highly suitable light module for examinations with the endoscope. The light of the light module is brought to the distal tip unit of the endoscope via the at least one light guiding element. The use of the light module advantageously provides good light transfer efficiency between the light module and the distal tip unit of the endoscope. Especially, the light module provides good light transfer efficiency between the light emitting devices and the light guiding element. Furthermore, the use of the light module advantageously ensures that enough space for cooling elements or portions is available in the light module to avoid overheating of the light module during operation.

The present disclosure further relates to an endoscopic system comprising: a light module as described above and an endoscope. The endoscope comprises an endoscope handle or interface and an insertion cord connected to the endoscope handle or interface. The insertion cord is configured to be inserted into a patient's body cavity and comprises a distal tip unit. The endoscopic system further comprises a display unit connected to the endoscope. The at least one light guiding element is configured to guide light towards the distal tip unit of the insertion cord of the endoscope.

The endoscope comprising an endoscope handle or interface means that a position interface may be provided functioning to control the position of the insertion cord. A handle, which can be grabbed by the user with his hands, is an example of a position interface. However, a position interface different from the handle may be provided which may e.g. be connectable to a robotic arm, i.e. "interface" may mean an interface for the robotic arm.

In other words, the light module may be a part of and/or integrated in the endoscope handle or interface. Alternatively, the light module may be an external light module which is integrated in the display unit and/or may be a part of a separate external module.

According to one preferred embodiment, the light module may be provided in the display unit. The light guiding element may be inserted into the endoscope via a port or connector provided at the endoscope handle or interface. The light guiding element may be guided through the endoscope handle or interface and through the insertion cord towards the distal tip unit of the same. Providing the light module in the display unit has the advantage that the coupling element and/or the cooling elements or portions may be designed in bigger or greater dimensions in the display unit.

The display unit may comprise (potentially in addition to the light module) a processor, a memory, including a graphical user interface (GUI) logic, an image processing device like a CPU or a FPGA, which may communicate with an image sensor provided at the distal tip unit via communication bus. The display unit may further comprise a video output board, a user interface, a microphone, a monitor, an electrical power supply, etcetera.

According to another preferred embodiment, the light module may be provided inside the endoscope handle or interface. In this case, the light module may be designed so as to fit into the endoscope handle or interface. Overheating of the light module is less critical in the handle or interface compared to the distal tip unit of the insertion cord of the endoscope, as heat may be better dissipated and not in direct contact with a patient during the procedure. Furthermore, the endoscope handle or interface may provide more space for additional cooling elements or portions than the distal tip unit. Positioning of the light module in the endoscope handle or interface preferably does not require an additional external light module provided e.g. in the display unit or separate lighting elements in the distal tip unit. In case the light module is positioned in the endoscope handle or interface, the light guiding element may extend from and through the endoscope handle or interface and through the insertion cord towards the distal tip unit of the same.

Preferably, the endoscopic system comprises a monitor connected to the endoscope, the monitor may be comprised in the display unit or being separate from and connected to the display unit. The monitor may function as an output device displaying information, e.g. images or videos for the user. The monitor may be a touchscreen. In this case, the monitor may functions as both an input and output device for the user. The monitor may be a part of the display unit. In case the monitor is separate from the display unit and is an external part, the monitor may be connected to the display unit. The display unit may be a portable display unit. The display unit may be operable to receive image data from an image sensor of a medical visualization device such as an endoscope and cause a display to display a live representation of the image data.

BRIEF DESCRIPTION OF THE DRAWINGS

The disclosure is explained in more detail below using preferred embodiments and referring to the accompanying figures.

The figures are schematic in nature and serve only to understand the disclosure. The features of the different embodiments can be interchanged among each other.

DETAILED DESCRIPTION OF THE FIGURES

Figure 1:
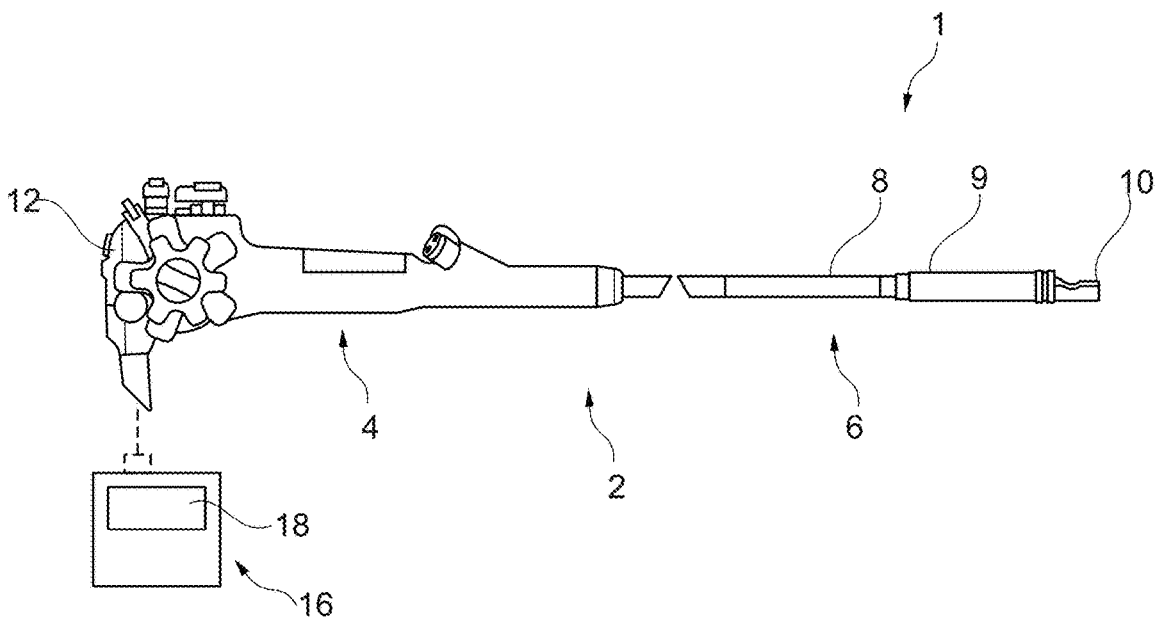
FIG. 1 shows a side view of an endoscopic system according to an embodiment of the present disclosure.
Figure 2:
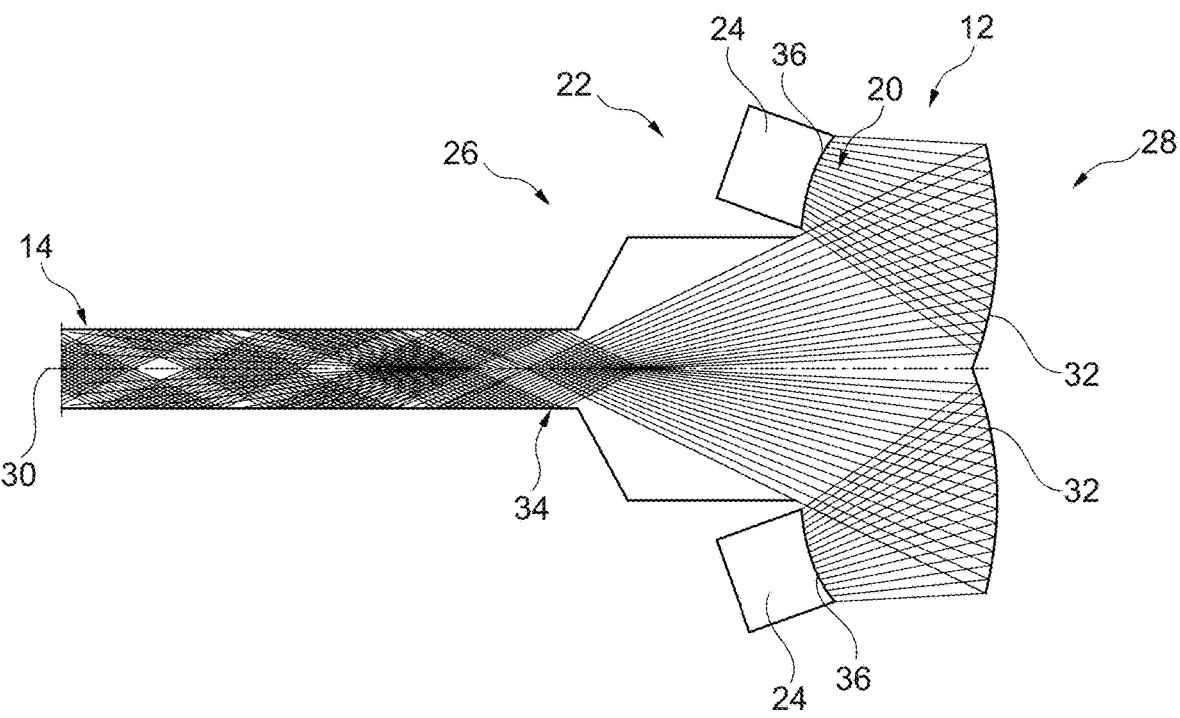
FIG. 2 shows a schematic view of a light module according to the present disclosure.

FIG. 1 shows a side view of an endoscopic system 1 according to an embodiment of the present disclosure. The endoscopic system 1 comprises an endoscope 2, which is preferably a single-use endoscope. The endoscope 2 comprises a handle 4 and an insertion cord 6 extending distally from the handle 4. The insertion cord 6 is configured to be inserted into a patient's body cavity and comprises an insertion tube 8, a bending section 9 and a distal tip unit 10. The endoscope 2 further comprises a light module 12. According to the embodiment shown in FIG. 1 the light module 12 is integrated in, i.e. is part of the handle 4. A light guiding element 14, as seen in FIG. 2, extends from the light module 12 into the insertion cord 6 and to the distal tip unit 10. The light provided by the light module 12 is therefore guided through the light guiding element 14 to the distal tip unit 10 of the endoscope 2 in order to illuminate the patient's body cavity. The endoscopic system 1 further comprises a display unit 16 comprising a monitor 18. The monitor 18 may alternatively be an external monitor outside of the display unit 16. The monitor 18 may display pictures or videos taken by an image sensor provided in the distal tip unit 10. The monitor 18 may be a touchscreen functioning as an input and output device for the operator. The display unit 16 and the monitor 18 may be connected to the endoscope 2 via a cable or wirelessly.

Figures 4, 5:
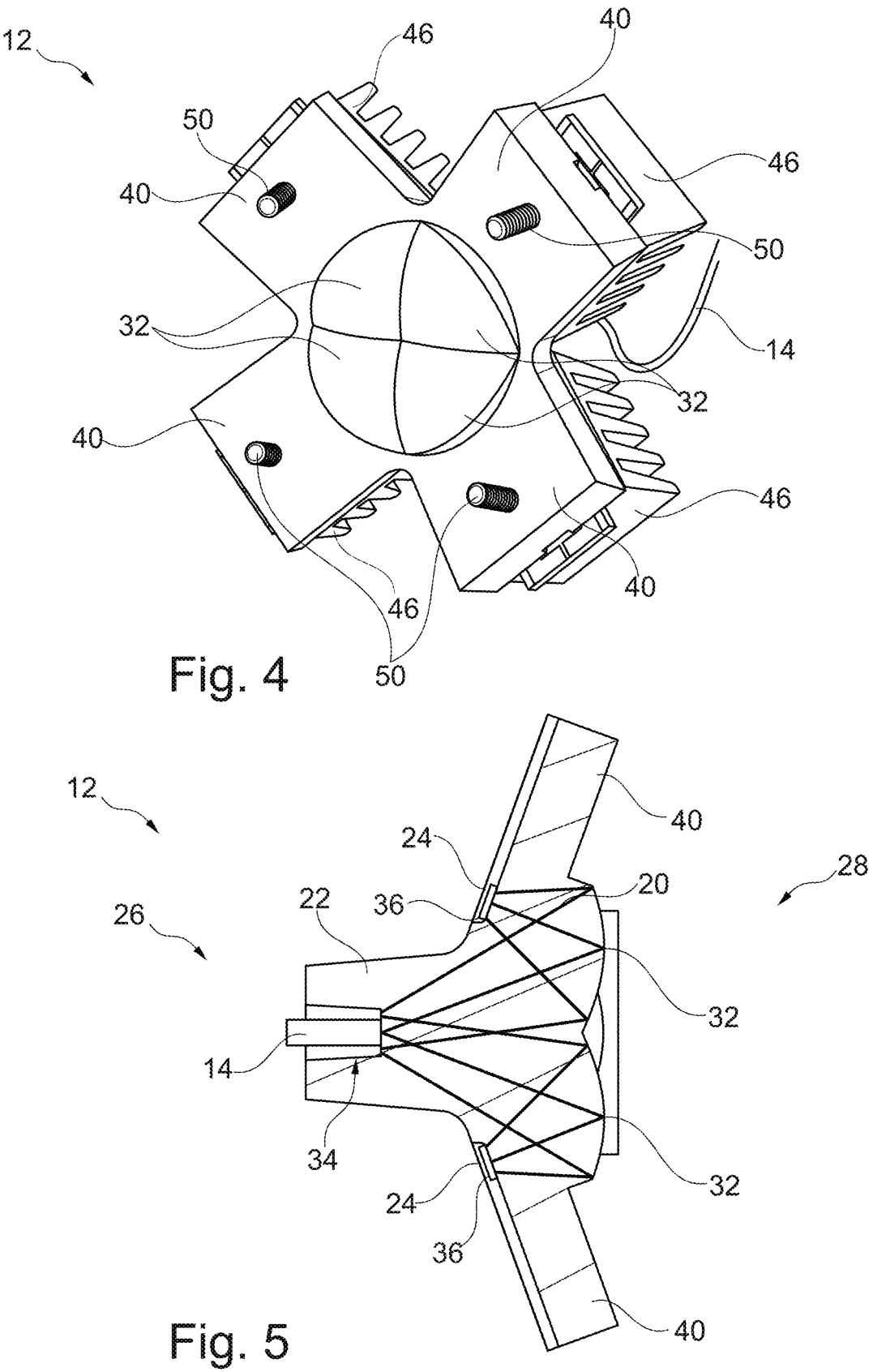
FIG. 4 shows an isometric view of a proximal side of the light module according to the first embodiment of the present disclosure.
FIG. 5 shows a longitudinal sectional view through the light module according to the first embodiment of the present disclosure.

FIG. 2 shows a schematic view of light rays 20 emitted by light emitting devices 24 in the light module 12 according to the present disclosure. The light module 12 comprises a coupling element 22 and a plurality of light emitting devices 24. The light emitting devices 24 may be connected to, e.g. attached to the coupling element 22. The coupling element 22 has a distal side 26 and a proximal side 28. The light emitting devices 24 are arranged on the distal side 26 of the coupling element 22. The light emitting devices 24 are positioned on a circle around a central axis 30 of the coupling element 22. The light emitting devices 24 emit light in the proximal direction towards a plurality of mirror elements or portions 32. The mirror elements or portions 32 are positioned on the proximal side 28 of the coupling element 22 and their centers may also be positioned on a circle around the central axis 30 of the coupling element 22. The mirror elements or portions 32 reflect the light emitted by the light emitting devices 24 towards a light receiving portion of the coupling element 22 and into the light guiding element 14. The light guiding element 14 is connected to the coupling element 22 at the distal side 26 of the coupling element 22, with a receiving portion 34 of the light guiding element 14 positioned on the central axis 30. Therefore, the light emitting devices 24 and the light guiding element 14 are both positioned on the side of the coupling element 22 which is opposite from the mirror elements or portions 32. The mirror elements or portions 32 are e.g. parabolic mirror elements or portions focusing the reflected light in a focal point or area of focus. The receiving portion 34 of the light guiding element 14 is in particular positioned at the focal point or area of focus of the mirror elements or portions 32. The light guiding element 14 guides the light from the light module 12 to the distal tip unit 10. The receiving portion 34 of the light guiding element 14 may be received in a cavity at the light receiving portion of the coupling element 22, as shown in FIG. 5.

More concretely, the light emitted by a light emitting device 24 is collimated by a collimator element or portion 36 before it is reflected by a mirror element or portion 32. By collimating the light before reflecting it, more light reaches the mirror elements or portions 32 and therefore the receiving portion 34 of the light guiding element 14. The collimator elements or portions 36 are preferably spherical geometries or convex or converging lenses directing the light rays 20 passing through the collimator elements or portions 36 in a parallel direction or close to a parallel direction, i.e. (slightly) focusing the light rays 20 towards the mirror elements or portions 32. The collimator elements or portions 36 are preferably positioned adjacent to the light emitting devices 24 and are preferably formed integrally with the coupling element 22, i.e. are preferably formed as collimator portions 36. The light rays 20 emitted by the light emitting devices 24 and collimated by the collimator elements or portions 36 are reflected by the mirror elements or portions 32 and are focused towards the light receiving portion of the coupling element 22 and into the receiving portion 34 of the light guiding element 14. In one example, a collimator element is provided as a lens or surface of the LED. In another example, the collimator element is a convex surface of the coupling element 22. In a further example, the coupling element 22 is devoid of the collimator elements; the LEDs may comprise surfaces matching corresponding surface areas of the coupling element 22 but without materially focusing the light or narrowing the light beam. Such an example may be suitable when the distance between the LED and the mirror surface is sufficiently small or when the loss of light, due to lack of narrowing, is acceptable.

According to the present disclosure, each light emitting device 24 of a plurality of light emitting devices 24 emits its light through a specific or own collimator element or portion 36 (for each light emitting device 24) onto a specific or own mirror element or portion 32 (for each light emitting device 24). The plurality of mirror elements or portions 32 reflects and directs the light emitted by the plurality of light emitting devices 24 and collimated by the plurality of collimator elements or portions 36 into at least one single light guiding element 14.

The light guiding element 14 is a light guide or light fiber as known in the art. When the light is reflected by the mirror elements or portions 32 and enters the light guiding element 14 centrally, the light rays 20 have a certain entry angle. The light rays 20 are then reflected at a boundary between a transparent core of the light guiding element 14 with a high refractive index and a cladding of the light guiding element 14 with a low refractive index by total internal reflection. The transparent core of the light guiding element 14 may be made either from glass or a synthetic material like polymethylmethacrylate (PMMA) or polycarbonate (PC). The light may be mixed in the light guiding element 14. More concretely, colored light emitted by the plurality of light emitting devices 24 may be mixed in the light guiding element 14 to provide uniformly mixed light at the distal tip unit 10. The uniformly mixed light emitted at the distal tip unit 10 may e.g. be white or a combination of blue and green wavelengths. Because of the length of the light guiding element 14, the light emitted at the distal tip unit 10 may appear to be white to the operator. There may alternatively be provided at least one light emitting device 24 emitting white light and at least one light emitting device 24 emitting a colored light of a specific wavelength. In this case, it is not necessary to mix light in order to receive white light, as the white light can be provided by the at least one white light LED.

Figure 3:
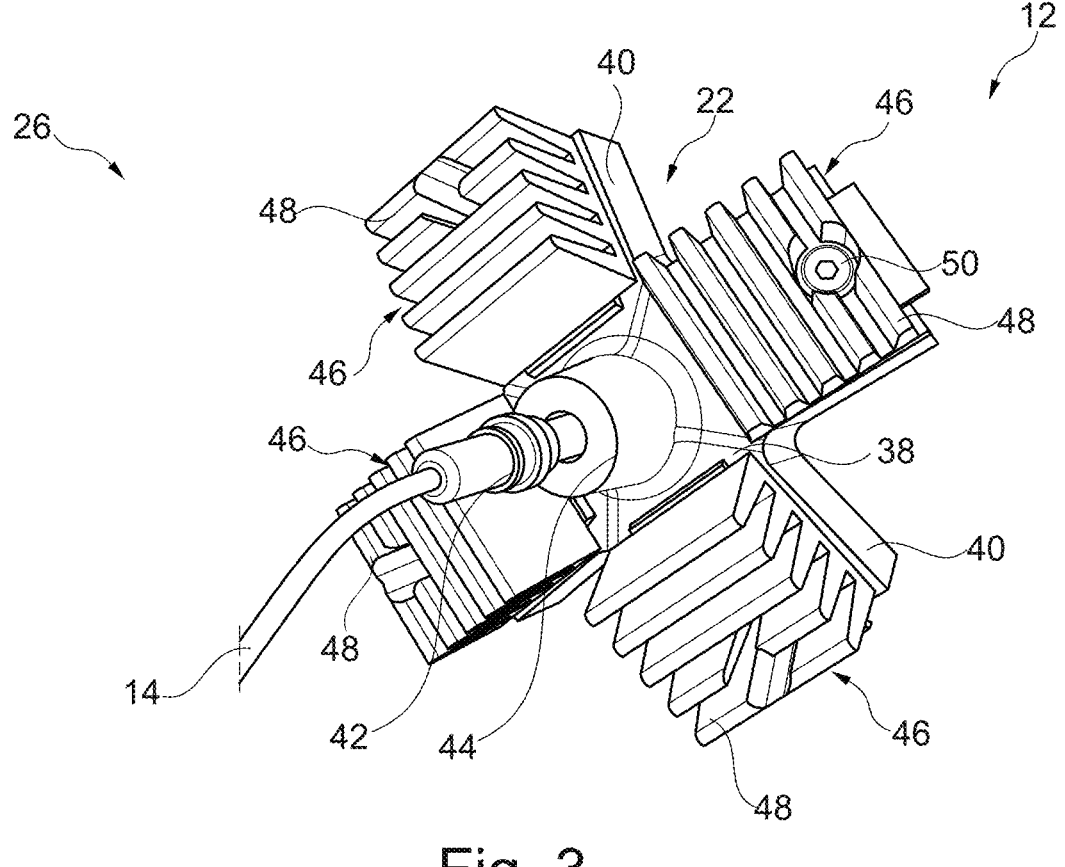
FIG. 3 shows an isometric view of a distal side of a light module according to a first embodiment of the present disclosure.

FIG. 3 shows an isometric view of the distal side 26 of a light module 12 according to a first embodiment of the present disclosure. FIG. 4 shows an isometric view of a distal side 26 of the light module 12 according to the first embodiment of the present disclosure. FIG. 5 shows a longitudinal sectional view through the light module 12 according to the first embodiment of the present disclosure.

The light module 12 comprises the coupling element 22 comprising a main body portion 38 and four arm portions 40 extending away from the main body portion 38 in different directions. The light guiding element 14 extends from a center of the main body portion 38 and is connected via a connector 42 to a protruding connecting portion 44 of the main body portion 38. Four light emitting devices 24 are provided, wherein a first light emitting device 24 is connected, e.g. attached to a first arm portion 40, a second light emitting device 24 is connected, e.g. attached to a second arm portion 40, a third light emitting device 24 is connected, e.g. attached to a third arm portion 40 and a fourth light emitting device 24 is connected, e.g. attached to a fourth arm portion 40. The four light emitting devices 24 are arranged on a circle around the central axis 30 and are equally spaced in the circumferential direction of the coupling element 22. The coupling element 22 is made from a transparent material, in particular a transparent thermoplastic polymer material, and is preferably manufactured via injection molding. Alternatively, the coupling element 22 could be manufactured from glass. The light emitting devices 24 can shine or emit light into the material of the coupling element 22. The coupling element 22 comprises four collimator elements or portions 36 adjacent to/in contact with the light emitting devices 24 on the distal side 26 and four mirror elements or portions 32 centrally on the proximal side 28 of the coupling element. Each light emitting device 24 has thus its own or specific collimator element or portion 36 and its own or specific mirror element or portion 32. The mirror elements or portions 32, in particular their centers, are arranged on a circle around the central axis 30. The four mirror elements or portions 32 are arranged directly adjacent each other in the circumferential direction and have approximately a quarter circle shape so as to form one complete circle in combination. The mirror elements or portions 32 are e.g. formed by providing a thin film or coating, e.g. via physical vapor deposition, onto the coupling element 22. The collimator elements or portions 36 are e.g. formed as collimator portions 36 being integral portions of the coupling element 22. Said differently, the transparent coupling element 22 may be formed in portions such that the collimator portions 36 collimating the light emitted by the light emitting devices 24 are provided.

The light emitting devices 24 positioned on the distal side 26 of the coupling element 22 and connected to the protruding arm portions 40 thus emit light through the collimator elements or portions 36 into the inside of the coupling element 22 towards the mirror elements or portions 32. The emitted light first passes the collimator elements or portions 36 and then passes through the transparent coupling element 22. The mirror elements or portions 32 arranged at the proximal side 28 of the coupling element 22 reflect the light towards the receiving portion 34 of the light guiding element 14. The mirror elements or portions 32 are parabolic mirrors focusing the light onto and into the receiving portion 34. It is to be understood that the light module 12 is not limited to having four protruding arm portions 40, four light emitting devices 24, four collimator elements or portions 36 and four mirror elements or portions 32. The light module 12 may comprise any number of protruding arm portions 40, light emitting devices 24, collimator elements or portions 36 and mirror elements or portions 32. Moreover, it is to be understood that even in case there are provided four protruding arm portions 40, four collimator elements or portions 36 and four mirror elements or portions 32, it is not necessary to attach four light emitting devices 24 to the coupling element 22. Said differently, the coupling element 22 shown in FIG. 3, FIG. 4 and FIG. 5 may alternatively be used with e.g. two or three light emitting devices 24.

The light module 12 shown in FIG. 3, FIG. 4 and FIG. 5 comprises cooling elements or portions 46 configured to cool the light module 12, in particular the light emitting devices 24. The cooling elements or portions 46 are positioned at the distal side 26 of the coupling element 22 and are positioned adjacent to the light emitting devices 24. Every light emitting device 24 comprises one cooling element or portion 46. The cooling elements or portions 46 comprise a number cooling ribs 48. Preferably, the cooling elements or portions 46 cool the light emitting devices 24 that generate heat during emission of light. The cooling elements or portions 46 are attached to the coupling element 22 via bolts 50 that extend through the protruding arm portions 40 of the coupling element 22. Other means of attachment of the cooling elements to the coupling element are also possible e.g. glue, circlips, geometrically locking geometry etc.

Figure 6:
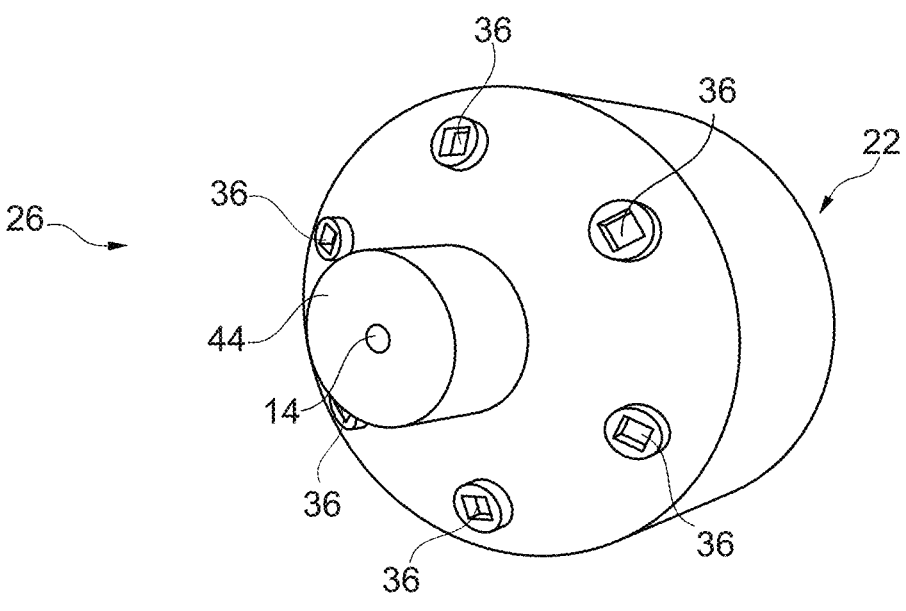
FIG. 6 shows an isometric view of a distal side of a coupling element of a light module according to a second embodiment of the present disclosure.

FIG. 6 shows an isometric view of a distal side 26 of a coupling element 22 of a light module 12 according to a second embodiment of the present disclosure. The general principle of the reflection of the emitted light towards the light guiding element 14 is the same as in the previous embodiments. The coupling element 22 is rotationally symmetric and is made from a transparent material as a single integral part. At the distal side 26, the coupling element 22 comprises the protruding connecting or receiving portion 44 for the light guiding element 14. The light guiding element 14 is arranged on the central axis 30 of the coupling element 22 and extends from the coupling element 22 towards the distal tip unit 10 of the endoscope 2. The coupling element 22 comprises a number of receiving portions for the light emitting devices 24 that function as the collimator elements or portions 36. The collimator elements or portions 36 are preferably arranged rotationally symmetric around the central axis 30 and are spaced from each other in a circumferential direction of the coupling element 22. The light emitting devices 24 emit their light into the coupling element 22 through the collimator elements or portions 36. There is one collimator element or portion 36 for each light emitting device 24. The light emitting devices 24 are positioned on the outer side surface of the coupling element 22. The collimator elements or portions 36 are designed as spherical geometries or lenses. The spherical geometries or lenses are configured so as to focus the light emitted by the light emitting devices 24. Therefore, the spherical geometries are preferably formed convexly.

The collimator elements or portions 36 are preferably formed as an integral part of the coupling element 22 and are thus preferably collimator portions 36. This is possible since the coupling element 22 is manufactured from the transparent material as a monolithic structure. The coupling element 22 is preferably manufactured by injection molding. Surfaces of the coupling element 22 except for the collimator elements or portions 36 may be overcoated after the manufacturing of the coupling element 22.

Figure 7:
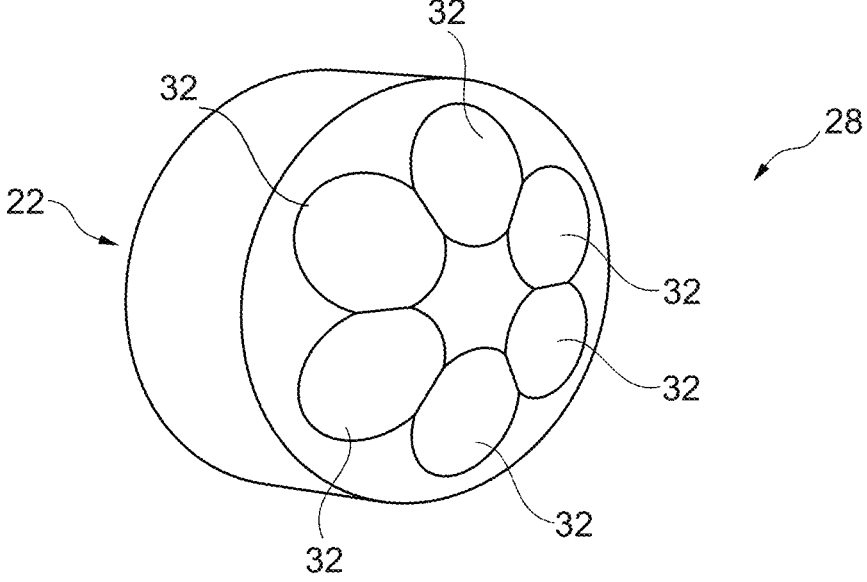
FIG. 7 shows an isometric view of a proximal side of the coupling element of the light module according to the second embodiment of the present disclosure.

FIG. 7 shows an isometric view of a proximal side 28 of the coupling element 22 of the light module 12 according to the second embodiment. The mirror elements or portions 32 are arranged or positioned on the proximal side 28 of the coupling element 22 opposite of the light emitting devices 24 and reflect the light towards the light guiding element 14. The mirror elements or portions 32 are spherical geometries that reflect the light emitted by the light emitting devices 24. The spherical geometries are preferably manufactured as an integral part of the coupling element 22 during the injection molding of the coupling element 22. The mirror elements or portions 32 are manufactured as thin films or coatings on the spherical, parabolic, and/or elliptic geometry of the coupling element 22. The mirror elements or portions 32 may be manufactured e.g. by physical vapor deposition. The thin films or coatings for the mirror elements or portions 32 are preferably applied after the injection molding of the spherical geometries. Therefore, the collimator elements or portions 36 as well as the mirror elements or portions 32 are both formed integrally with the coupling element 22. The number of light emitting devices 24 may be varied, and it may be provided that not all receiving portions for the light emitting devices 24 are provided with light emitting devices 24.

Figure 8:
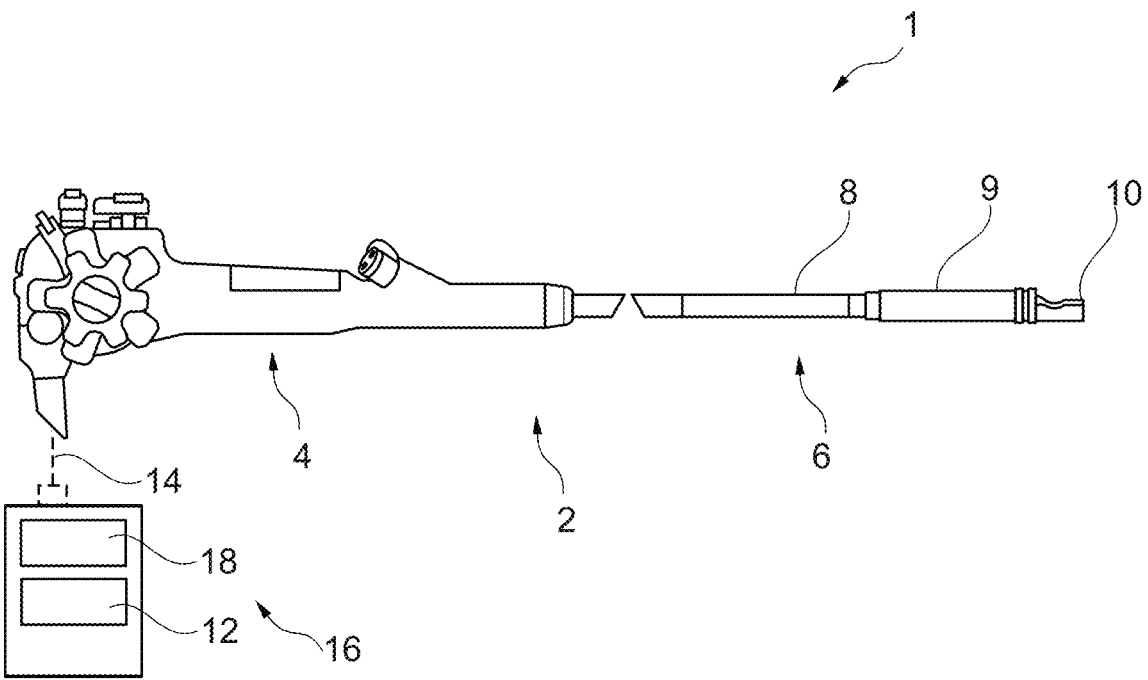
FIG. 8 shows a side view of an endoscopic system according to another embodiment of the present disclosure.

FIG. 8 shows a side view of an endoscopic system 1 according to another embodiment. The endoscope 2 comprises the handle or interface 4 and the insertion cord 6. According to the embodiment of FIG. 8, the light module 12 is not part of the handle 4, but is provided in the display unit 16. The display unit 16 may also comprise the monitor 18. The light guiding element 14 extends from the light module 12 into and through the handle 4 and the insertion cord 6 towards the distal tip unit 10. The display unit 16 may further comprise a processor, a memory, including a graphical user interface (GUI) logic, an image processing device like a CPU or a FPGA, which may communicate with an image sensor provided at the distal tip unit 10 via communication bus. The display unit 16 may further comprise a video output board, a user interface, a microphone, a monitor, and an electrical power supply (not shown). Example display units, also known as video processing apparatus, are described in commonly owned U.S. Pat. Nos. 11,109,741 and 11,583,164, both incorporated by reference herein in their entirety.

Embodiments of the present disclosure, variations thereof, and examples thereof are set out in the following items:

1. Light module (12) for an endoscopic system (1), the light module (12) comprising: a coupling element (22); at least one light guiding element (14) connected to the coupling element (22) and configured to guide light towards a distal tip unit (10) of an endoscope (2) comprised in the endoscopic system (1); a plurality of light emitting devices (24) connected to the coupling element (22) and configured to emit light; a plurality of collimator elements or portions (36) configured to collimate the light emitted by the plurality of light emitting devices (24); a plurality of mirror elements or portions (32) configured to reflect the light emitted by the plurality of light emitting devices (24) and collimated by the plurality of collimator elements or portions (36) towards and into the at least one light guiding element (14); wherein the light module (12) is designed such that each light emitting device (24) of the plurality of light emitting devices (24) emits its light through a specific or own collimator element or portion (36) onto a specific or own mirror element or portion (32), and that the plurality of mirror elements or portions (32) reflects and directs the light emitted by the plurality of light emitting devices (24) into the at least one light guiding element (14).

2. Light module (12) according to claim 1, wherein the coupling element (22) has a proximal side (28) and a distal side (26); the plurality of light emitting devices (24) and the at least one light guiding element (14) are provided on the proximal side (28) of the coupling element (22); the plurality of mirror elements or portions (32) is provided on the distal side (26) of the coupling element (22); the plurality of light emitting devices (24) is configured to emit light in a proximal direction towards the plurality of mirror elements or portions (32); and the plurality of mirror elements or portions (32) is configured to reflect the light in a distal direction towards the at least one light guiding element (14).

3. Light module (12) according to claim 1 or 2, wherein the coupling element (22) is a single and integral transparent part, preferably a polymer part, especially preferred a molded polymer part.

4. Light module (12) according to any one of the preceding claims 1 to 3, wherein the collimator elements or portions (36) are formed as collimator portions integrally provided in the coupling element (22).

5. Light module (12) according to any one of the preceding claims 1 to 4, wherein the mirror elements or portions (32) are formed as thin films or coatings provided on the coupling element (22).

6. Light module (12) according to any one of the preceding claims 1 to 5, wherein the coupling element (22) comprises a central axis (30) and the at least one light guiding element (14), in particular a receiving portion (34) of the at least one light guiding element (14) connected to the coupling element (22), is arranged on the central axis (30).

7. Light module (12) according to claim 6, wherein the light emitting devices (24) are arranged around the central axis (30) and are spaced in a circumferential direction of the coupling element (22).

8. Light module (12) according to claim 7, wherein the light emitting devices (24) are arranged on a first circle around the central axis (30) and are equally spaced in the circumferential direction of the coupling element (22).

9. Light module (12) according to any one of claims 6 to 8, wherein the mirror elements or portions (32) are arranged on a second circle around the central axis (30).

10. Light module (12) according to claim 9, wherein the mirror elements or portions (32) are equally spaced in the circumferential direction of the coupling element (22) or are arranged directly adjacent to each other in the circumferential direction of the coupling element (22).

11. Light module (12) according to any one of the preceding claims 1 to 10, further comprising cooling elements or portions (46) arranged at or connected to the coupling element (22), the cooling elements or portions (46) being configured to cool the light module (12), in particular the plurality of light emitting devices (24).

12. Light module (12) according to any one of the preceding claims 1 to 11, wherein the light emitting devices (24) are light emitting diodes and wherein the light emitting diodes comprise at least one white light emitting diode and at least one colored light emitting diode.

13. Use of a light module (12) according to any one of the preceding claims 1 to 12 in an endoscopic system (1) comprising an endoscope (2) having an handle (4) or interface and a display unit (16) connected to the endoscope (2).

14. Endoscopic system (1) comprising: a light module (12) according to any one of the preceding claims 1 to 12; an endoscope (2) comprising: an handle (4) or interface; and an insertion cord (6) connected to the handle (4) or interface, configured to be inserted into a patient's body cavity and comprising a distal tip unit (10); and a display unit (16) connected to the endoscope (2); and wherein the at least one light guiding element (14) is configured to guide light towards the distal tip unit (10) of the insertion cord (6) of the endoscope (2).

15. Endoscopic system (1) according to claim 14, further comprising a monitor (18) connected to the endoscope (2), the monitor (18) either being comprised in the display unit (16) or being separate from and connected to the display unit (16).

Although some embodiments have been described and shown in detail, the invention is not restricted to them, but may also be embodied in other ways within the scope of the subject matter defined in the following items. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

The terms "comprises/comprising," "includes/including," "having/have," and derivatives thereof are inclusive transition terms that describe the presence of stated features, integers, steps or components but do not preclude the presence or addition of one or more other features, integers, steps, components or groups thereof.

LIST OF REFERENCE SIGNS

1 endoscopic system
2 endoscope
4 handle
6 insertion cord
8 insertion tube
9 bending section
10 distal tip unit
12 light module
14 light guiding element
16 display unit
18 monitor
20 light ray
22 coupling element
24 light emitting device
26 distal side
28 proximal side
30 central axis
32 mirror element or portion
34 receiving portion
36 collimator element or portion
38 main body portion

40 arm portion
42 connector
44 connecting portion
46 cooling element or portion
48 cooling rib
50 bolt

We claim:

1. A light module comprising:
a coupling element being a single and integral part comprised of a transparent material, the coupling element including a main body portion, a proximal side, a distal side, a plurality of collimator elements or portions formed on the distal side, and a plurality of convex surfaces formed on the proximal side, the main body portion including a common light receiving portion, plurality of collimator elements or portions being arranged around the common light receiving portion;
at least one light guiding element aligned with the common light receiving portion;
a plurality of light emitting devices mounted onto an outside surface of the coupling element and on the distal side of the coupling element, the plurality of light emitting devices being configured to emit light through the plurality of collimator elements or portions and through the transparent material to the plurality of convex surfaces;
a plurality of mirror elements or portions configured to reflect the light emitted by the plurality of light emitting devices and collimated by the plurality of collimator elements or portions towards and into the at least one light guiding element, the plurality of mirror elements or portions comprising thin films or coatings on the plurality of convex surfaces of the coupling element,
wherein each light emitting device of the plurality of light emitting devices emits its light through a specific or own collimator element or portion onto a specific or own mirror element or portion, and wherein the plurality of mirror elements or portions reflects and directs the light emitted by the plurality of light emitting devices through the transparent material and into the common light receiving portion.

2. The light module of claim 1, wherein the coupling element further comprises arm portions extending from the main body portion, wherein each of the plurality of light emitting devices is mounted on one of the arm portions, and wherein the main body portion is adapted to connect the at least one light guiding element, the at least one light guiding element thereby receiving the light from the common light receiving portion.

3. The light module of claim 2, further comprising heat-sinks, each heat-sink thermally coupled to one of the plurality of light emitting devices, wherein the heat-sinks are arranged on the arm portions around a central axis traversing the common light receiving portion.

4. The light module of claim 1, wherein the coupling element is a polymer part.

5. The light module of claim 1, wherein the coupling element comprises a central axis, wherein the coupling element is adapted to connect the at least one light guiding element, and wherein a receiving portion of the at least one light guiding element is connected to the coupling element and arranged on the central axis, the at least one light guiding element thereby receiving light from the common light receiving portion.

6. The light module of claim 1, wherein the coupling element comprises a central axis, and wherein the plurality of light emitting devices are arranged around the central axis and are spaced in a circumferential direction of the coupling element.

7. The light module of claim 6, wherein the plurality of light emitting devices are arranged on a first circle around the central axis and are equally spaced in the circumferential direction of the coupling element.

8. The light module of claim 7, wherein the plurality of mirror elements or portions are arranged on a second circle around the central axis.

9. The light module of claim 8, wherein the plurality of mirror elements or portions are equally spaced in the circumferential direction of the coupling element or are arranged directly adjacent to each other in the circumferential direction of the coupling element.

10. The light module of claim 1, further comprising cooling elements or portions arranged at or connected to the coupling element, the cooling elements or portions being configured to cool the light module.

11. The light module of claim 1, wherein the plurality of light emitting devices comprise a white light emitting diode and a colored, non-white, light emitting diode.

12. An endoscopic system comprising:
the light module of claim 1;
the at least one light guiding element connected to the coupling element of the light module; and
an endoscope comprising:
a handle or interface; and
an insertion cord connected to the handle or interface and including a distal tip unit,
wherein the at least one light guiding element extends through the insertion cord to guide the light toward the distal tip unit.

13. The endoscopic system of claim 12, wherein the plurality of light emitting devices and the coupling element are positioned in the handle or interface.

14. The endoscopic system of claim 13, further comprising a display unit connectable to the endoscope.

15. The endoscopic system of claim 12, further comprising a display unit connected to the endoscope, wherein the plurality of light emitting devices and the coupling element are positioned in the display unit, and wherein the at least one light guiding element extends from the display unit through the insertion cord.

16. An endoscope comprising:
a handle or interface;
an insertion cord connected to the handle or interface and including a distal tip unit;
at least one light fiber or light guide; and
the light module of claim 1.

17. The endoscope of claim 16, wherein the coupling element further comprises convex surfaces on the distal side, each of the convex surfaces positioned between a light emitting diode and a corresponding reflective surface, wherein in use the light emitted by the light emitting diode passes through the convex surface and is reflected by the reflective surface toward the common light receiving portion.

18. The endoscope of claim 16, wherein the coupling element further comprises a main body portion and arm portions extending from the main body portion, wherein each of the plurality of light emitting diodes is mounted on one of the arm portions.

19. The endoscope of claim 18, wherein the light emitting diodes comprise a white light emitting diode and a non-white light emitting diode.

* * * * *